United States Patent [19]

Hwang et al.

[11] Patent Number: 4,822,779
[45] Date of Patent: Apr. 18, 1989

[54] PHOSPHORIC AND THIOPHOSPHONIC ACID DERIVATIVES OF 5-HYDROXYPYRAZOLES, COMPOSITIONS AND USE

[75] Inventors: Ki J. Hwang; Yeong D. Gong; Gil H. Kim, all of Daejeon, Rep. of Korea

[73] Assignee: Korea Research Institute of Chemical Technology, Chungcheongnam, Rep. of Korea

[21] Appl. No.: 233,098

[22] Filed: Aug. 15, 1988

[30] Foreign Application Priority Data

Mar. 26, 1988 [KR] Rep. of Korea ............... 88-3318

[51] Int. Cl.[4] ............... A01N 57/16; C07F 9/09; C07F 9/165

[52] U.S. Cl. ............... 514/94; 548/116; 548/375; 548/376

[58] Field of Search ............... 548/116, 375, 376; 514/94

[56] References Cited

U.S. PATENT DOCUMENTS 4,466,962  8/1984  Aoyagi et al. ............... 548/116

Primary Examiner—Robert W. Ramsuer
Attorney, Agent, or Firm—Finnegan, Henderson, Farabow, Garrett & Dunner

[57] ABSTRACT

5-hydroxypyrazole derivatives and the insecticidal compositions containing the same are provided. Said derivatives exhibit excellent insecticidal effects and bioactivities, and also they have a broad-spectrum of use.

17 Claims, No Drawings

PHOSPHORIC AND THIOPHOSPHONIC ACID DERIVATIVES OF 5-HYDROXYPYRAZOLES, COMPOSITIONS AND USE

BACKGROUND OF THE INVENTION

The present invention relates to novel 5-hydroxypyrazole derivatives which have active insecticidal properties. The present invention also relates to the insecticidal compositions comprising said derivatives and to the use of such compositions for the kill and control of insects.

Recently, pyrethroid insecticides have widely been used because of their excellent insecticidal effects, however, they have some disadvantages, namely they are costly, and they are liable to lose their effect in the air. Also, in the case of using the pyrethroid insecticides repeatedly for several years, the target insects develop a resistance to the chemicals, therefore, great quantities must be used in order to obtain the desired insecticidal effect.

Thus, it is proposed that pyrazole phosphoric esters instead of pyrethroid compounds be used as the insecticidal and miticidal agents in Korean patent publication No. 84-255. But, there is much room for improvement, for example, such pyrazole compounds don't exhibit good bioactivity and complete insecticidal effects against some insects such as brown plant hoppers and aphides, can not be expected, etc..

Therefore, with consideration to the foregoing points the present inventors have developed new insecticidal compounds having excellent bioactivities and a broad-spectrum of use.

SUMMARY OF THE INVENTION

An object of the present invention is to provide new 5-hydroxypyrazole derivatives which produce broad-spectrum and powerful insecticidal actions to even said insects.

Another object of the present invention is to provide the insecticidal compositions containing active compounds of said derivatives.

DETAILED DESCRIPTION OF THE INVENTION

The present invention is directed to phosphorus derivatives of 5-hydroxypyrazole which correspond to the following formula (I).

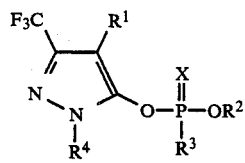

wherein
  $R^1$ represents hydrogen, or a halogen atom selected from the group consisting of bromine, chlorine and iodine;
  $R^2$ represents a lower alkyl group;
  $R^3$ represents an alkoxy, lower alkylthio, phenoxy or thiophenoxy group;
  $R^4$ represents hydrogen, a lower alkyl, or substituted or unsubstituted phenyl group; and
  X represents oxygen or sulfur.

In the present specification and claims, the term "lower alkyl" designates a straight or branched chain alkyl group of 1 to 6 carbon atoms.

According to the present invention, said 5-hydroxypyrazole derivatives can be easily prepared by esterification of the 5-hydroxypyrazole reactant shown by the following formula (II) or a salt thereof with a phosphorus reactant shown by the following formula (III) in the presence of an organic solvent and an acid-binding agent.

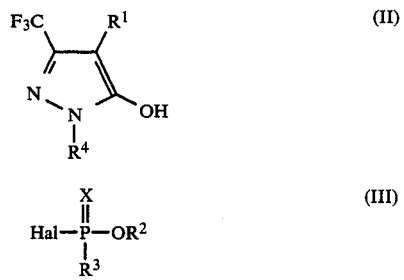

wherein, $R^1$, $R^2$, $R^3$, $R^4$ and X are as hereinbefore defined; and Hal represents a halogen atom.

More concretely, an appropriate 5-hydroxypyrazole (or its salt) reactant of the formula (II) is first mixed with an organic solvent and an acid-binding agent (an acid absorber), and then an appropriate phosphorus reactant of the formula (III) is added to the mixture so as to esterify the 5-hydroxypyrazole reactant.

As a result of the foregoing processes, the 5-hydroxypyrazole is easily esterified with the phosphorus compound to be converted into the object compound of the invention. The esterification is complete when all of the phosphorus reactant has been consumed. In the present invention, it is preferred to react substantially equimolar amounts of the 5-hydroxypyrazole reactant and the phosphorus reactant.

Representative organic solvents include, for example, acetonitrile, cyclohexane, benzene, toluene, xylene, acetone, methylene chloride, methylethyl ketone, diethylether, dioxane, tetrahydrofuran and the like.

Representative acid-binding agents include, for example, alkaline metal or alkali earth metal hydroxides, oxides, carbonates and bicarbonates; alkaline metal alcoholates; and tertiary amines.

After esterification according to the present invention, the completion of the reaction can be easily confirmed using known methods, for example, TLC and GC.

At the completion of the reaction, the reaction mixture is filtered to remove any insolubles, the collected filtrate is washed several times with water, and the solvent is removed under reduced pressure to leave the desired product, if necessary, the resultant product is purified by redistillation or chromatography.

Also, in the case of preparing a hydroxypyrazole derivative shown by the formula (I) having a halogen in $R^1$-position, if necessary, the object 5-hydroxypyrazole compound can be prepared by halogenation of a corresponding 5-hydroxypyrazole compound of the formula (I) having a hydrogen in the $R^1$-position, using a halogenation agent such as N-bromosuccinimide(NBS), N-chlorosuccinimide(NCS), dimethyldichlorohydantoin, sulfurylchloride or thionylchloride.

New 5-hydroxypyrazole derivatives shown by the formula (I) of the present invention are listed in Table 1.

TABLE 1

| Compound No. | R¹ | R² | R³ | R⁴ | X |
|---|---|---|---|---|---|
| 1 | H | C₂H₅ | OC₂H₅ | H | O |
| 2 | H | C₂H₅ | OC₂H₅ | H | S |
| 3 | H | CH₃ | OCH₃ | CH₃ | O |
| 4 | H | C₂H₅ | OC₂H₅ | CH₃ | O |
| 5 | H | C₂H₅ | SC₆H₅ | CH₃ | O |
| 6 | H | C₂H₅ | SC₃H₇(n) | CH₃ | O |
| 7 | H | CH₃ | OCH₃ | CH₃ | S |
| 8 | H | C₂H₅ | OC₂H₅ | CH₃ | S |
| 9 | H | C₂H₅ | SC₆H₅ | CH₃ | S |
| 10 | H | C₂H₅ | SC₃H₇(n) | CH₃ | S |
| 11 | H | CH₃ | OCH₃ | C₆H₅ | O |
| 12 | H | C₂H₅ | OC₂H₅ | C₆H₅ | O |
| 13 | H | C₂H₅ | SC₆H₅ | C₆H₅ | O |
| 14 | H | CH₃ | OCH₃ | C₆H₅ | S |
| 15 | H | C₂H₅ | OC₂H₅ | C₆H₅ | S |
| 16 | H | C₂H₅ | SC₆H₅ | C₆H₅ | S |
| 17 | H | CH₃ | OCH₃ | 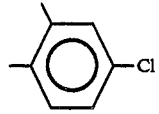 | O |
| 18 | H | C₂H₅ | OC₂H₅ | 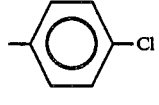 | O |
| 19 | H | CH₃ | OCH₃ | 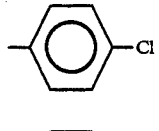 | S |
| 20 | H | C₂H₅ | OC₂H₅ | 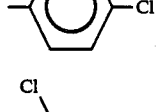 | S |
| 21 | H | CH₃ | OCH₃ | 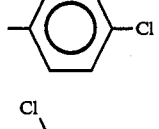 | O |
| 22 | H | C₂H₅ | OC₂H₅ | 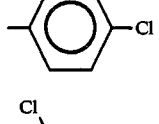 | O |
| 23 | H | CH₃ | OCH₃ | 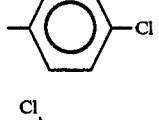 | S |
| 24 | H | C₂H₅ | OC₂H₅ | 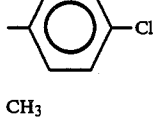 | S |
| 25 | Cl | CH₃ | OCH₃ | CH₃ | O |
| 26 | Cl | C₂H₅ | OC₂H₅ | CH₃ | O |
| 27 | Cl | C₂H₅ | SC₆H₅ | CH₃ | O |
| 28 | Cl | CH₃ | OCH₃ | CH₃ | S |
| 29 | Cl | C₂H₅ | OC₂H₅ | CH₃ | S |
| 30 | Cl | C₂H₅ | SC₆H₅ | CH₃ | S |
| 31 | Cl | C₂H₅ | SC₃H₇(n) | CH₃ | S |
| 32 | Cl | CH₃ | OCH₃ | C₆H₅ | O |
| 33 | Cl | C₂H₅ | OC₂H₅ | C₆H₅ | O |
| 34 | Cl | C₂H₅ | SC₆H₅ | C₆H₅ | O |
| 35 | Cl | CH₃ | OCH₃ | C₆H₅ | S |
| 36 | Cl | C₂H₅ | OC₂H₅ | C₆H₅ | S |
| 37 | Cl | C₂H₅ | SC₃H₇(n) | C₆H₅ | S |
| 38 | Cl | CH₃ | OCH₃ | 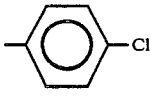 | O |
| 39 | Cl | C₂H₅ | OC₂H₅ | 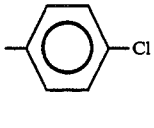 | O |
| 40 | Cl | C₂H₅ | OC₂H₅ | 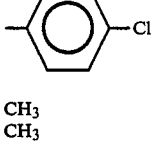 | S |
| 41 | Br | CH₃ | OCH₃ | CH₃ | O |
| 42 | Br | C₂H₅ | OC₂H₅ | CH₃ | O |
| 43 | Br | C₂H₅ | OC₂H₅ | CH₃ | S |
| 44 | Br | C₂H₅ | OC₂H₅ | C₆H₅ | O |
| 45 | Br | C₂H₅ | OC₂H₅ | C₆H₅ | S |
| 46 | Br | C₂H₅ | OC₂H₅ | 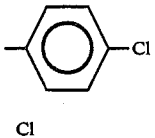 | S |
| 47 | Br | C₂H₅ | OC₂H₅ | 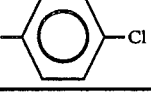 | S |

This invention is illustrated by the following Examples, but should not be construed to be limited thereto.

EXAMPLE 1

Preparation of O,O-dimethyl-O-(1-methyl-3-trifluoromethyl-5-pyrazoyl)phosphoric ester (Compound No. 3)

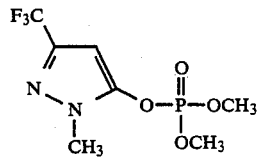

1.7 g (10 mmol) of 1-methyl-3-trifluoromethyl-5-hydroxy pyrazole, 1.60 g (11 mmol) of dimethylchlorophosphate and 1.1 g (11 mmol) of triethylamine were added to 10 ml of methylenechloride, and the mixture was stirred at room temperature for 2 hours. At the completion of the reaction, the reaction solution was filtered and the solvent was removed under reduced pressure. The resultant product was purified by column chromatography on silica-gel using a mixed solvent (4:1) of hexane and ethylacetate as a developing solvent, leaving 2.33 g (85% of theoretical) of the above-indicated product having a light yellow color.

¹H NMR(CDCl₃): δ=3.65 (s, 3H), 3.7 (s, 3H), 4.0 (s, 3H), 6.5 (s, 1H).

Mass: m/e=274

EXAMPLE 2

Preparation of O,O-diethyl-O-(1-methyl-3-trifluoromethyl-5-pyrazoyl)phosphoric ester (Compound No. 4)

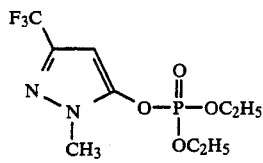

1.0 g of 1-methyl-3-trifluoromethyl-5-hydroxypyrazole, 1.24 g of diethylchlorophosphate and 0.72 g of triethylamine were added to 10 ml of methylenechloride, and the mixture was stirred at room temperature for 2 hours. At the completion of the reaction, the reaction solution was filtered and the solvent was removed under reduced pressure to obtain an oil-phase liquid. The resultant oil-phase liquid was purified by column chromatography on silica-gel using a developing solvent (4:1) of hexane and ethylacetate leaving 1.6 g of the above-indicated product having a light yellow color.

$^1$H NMR(CDCl$_3$): $\delta$=1.2 (t, 6H), 3.6 (s, 3H), 3.9 (q, 4H), 6.3 (s, 1H).

Mass: m/e=302.1

EXAMPLE 3

Preparation of O,O-dimethyl-O-(1-methyl-3-trifluoromethyl-5-pyrazoyl)thiophosphoric ester (Compound No. 7)

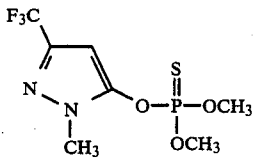

After 500 mg (3.0 mmol) of 1-methyl-3-trifluoromethyl-5-hydroxypyrazole, 830 mg (6.0 mmol) of potassium carbonate and 484 mg (3.0 mmol) of dimethylchlorothiophosphate were dissolved in acetonitrile, a little dimethylaminopyridine (DMAP) was added and reacted at room temperature for 6 hours. At the completion of the reaction, the reaction solution was filtered and the solvent was removed. The resultant product was purified by column chromatography on silica-gel using a developing solvent (9:1) of hexane and ethylacetate, leaving 680 mg (78% of theoretical) of the above-indicated product.

$^1$H NMR(CDCl$_3$): $\delta$=3.7 (s, 6H), 4.0 (s, 3H), 6.5 (s, 1H).

Mass: m/e=290

EXAMPLE 4

Preparation of O,O-diethyl-O-(1-methyl-3-trifluoromethyl-5-pyrazoyl)thiophosphoric ester (Compound No. 8)

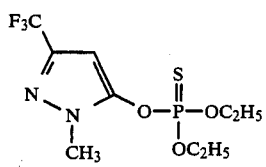

After 0.9 g of 1-methyl-3-trifluoromethyl-5-hydroxypyrazole, 1.02 g of diethylchlorothiophosphate and b 0.70 g of triethylamine were added methylenechloride, the resultant solution was reacted at room temperature for 4 hours with stirring. Hereinafter the procedure was the same as in Example 2, and 1.14 g of the colorless above-indicated product was obtained.

$^1$H NMR(CDCl$_3$): $\delta$=1.3 (t, 6H), 3.6 (s, 3H), 4.0 (q, 4H), 6.3 (s, 1H).

Mass: m/e=318.1

EXAMPLE 5

Preparation of O-ethyl-O-(1-methyl-3-trifluoromethyl-5-pyrazoyl)-S-phenylthiophosphoric ester (Compound No. 9)

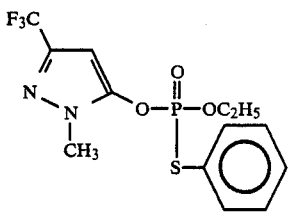

After 0.4 g (2.4 mmol) of 1-methyl-3-trifluoromethyl-5-hydroxypyrazole, 0.57 g (2.4 mmol) of O-ethyl-S-phenylchlorophosphate and 0.24 g (2.4 mmol) of triethylamine were dissolved in 10 ml of dichloromethane, the resultant solution was reacted at room temperature for 8 hours. At the completion of the reaction, the reaction solution was filtered and the solvent was removed. The resultant product was purified by column chromatography on silica-gel using a developing solvent (3:1) of hexane and ethylacetate to leave 0.44 g (50% of theoretical) of the aboveindicated product in a colorless liquid phase.

$^1$H NMR(CDCl$_3$): $\delta$=1.3 (t, 3H), (s, 3H), 4.2 (q, 2H), 6.2 (s, 1H). 7.1~7.4 (m, 5H).

Mass: m/e=377

Rf(ethylacetate/hexane=1:1)=0.3

EXAMPLE 6

Preparation of O,O-dimethyl-O-(1-phenyl-3-trifluoromethyl-5-pyrazoyl)phosphoric ester (Compound No. 11)

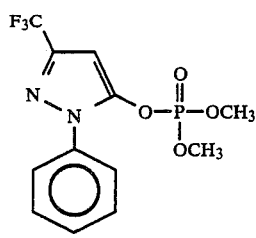

After 500 mg (2.2 mmol) of 1-phenyl-3-trifluoromethyl-5-hydroxypyrazole, 833 mg (6.02 mmol) of potassium carbonate and 320 mg (2.2 mmol) of dimethylchlorophosphate were dissolved in 15 ml of acetonitrile, a little dimethylaminopyridine (DMAP) was added and allowed to react at room temperature for 8 hours. Hereinafter the procedure was the same as in Example 5, and then 602 mg (82% of theoretical) of the above-indicated product was obtained.

$^1$H NMR(CDCl$_3$): $\delta$=3.8 (s, 6H), 6.4 (s, 1H), 7.5 (m, 5H).

Mass: m/e=336

EXAMPLE 7

Preparation of O,O-diethyl-O-(1-phenyl-3-trifluoromethyl-5-pyrazoyl)phosphoric ester (Compound No. 12)

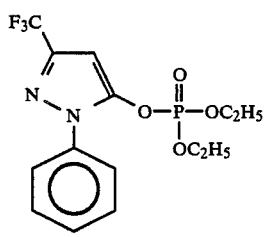

After 500 mg (2.19 mmol) of 1-phenyl-3-trifluoromethyl-5-hydroxypyrazole, 380 mg (2.19 mmol) of diethylchlorophosphate and 600 mg (4.4 mmol) of potassium chloride were dissolved in 15 ml of acetonitrile, the resultant solution was reacted at a temperature of 50° to 60° C. for 2 hours. After the completion of the reaction, the reaction solution was filtered and the solvent was removed under reduced pressure to leave an oilphase liquid. The resultant liquid was purified by column chromatography on silica-gel using a developing solvent (5:1) of hexane and ethylacetate, consequently, 590 mg (76% of theoretical) of the yellowish colored above-indicated product was obtained.

$^1$H NMR(CDCl$_3$): $\delta$=7.5 (m, 5H), 6.4 (s, 1H), 4.2 (q, 4H), 1.3 (t, 6H).

Mass: m/e=364

EXAMPLE 8

Preparation of O,O-dimethyl-O-(1-phenyl-3-trifluoromethyl-5-pyrazoyl)thiophosphoric ester (Compound No. 14)

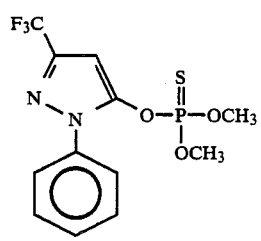

As a result of following the same method as in Example 3 except that 500 mg (2.2 mmol) of 1-phenyl-3-trifluoromethyl-5-hydroxypyrazole was used instead of 1-methyl-3-trifluoromethyl-5-hydroxypyrazole, 540 mg (70% of theoretical) of the above-indicated product was obtained.

$^1$H NMR(CDCl$_3$): $\delta$=3.65 (s, 3H), 3.7 (s, 3H), 6.3 (s, 1H), 7.4 (m, 5H).

Mass: m/e=351

EXAMPLE 9

Preparation of O,O-diethyl-O-(1-phenyl-3-trifluoromethyl-5-pyrazoyl)thiophosphoric ester (Compound No. 15)

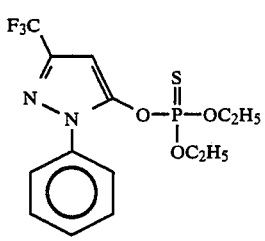

After 500 mg (2.19 mmol) of 1-phenyl-3-trifluoromethyl-5-hydroxypyrazole, 414 mg (2.19 mmol) of diethylchlorothiophosphate and 600 mg (4.4 mmol) of potassium carbonate were dissolved in 15 ml of acetonitrile, the resultant solution was reacted at a temperature of 50° to 60° C. for 2 hours. At the completion of the reaction, the reaction solution was filtered and the solvent was removed under reduced pressure to leave an oil-phase liquid. The resultant liquid was purified by column chromatography on silica-gel using a developing solvent (9:1) of hexane and ethylacetate. Consequently, 700 mg (84% of theoretical) of the yellowish colored above-indicated product was obtained.

$^1$H NMR(CDCl$_3$): $\delta$=7.5(m, 5H), 6.4(s, 1H), 4.2(q, 4H), 1.3(t, 6H).

Mass: m/e=380

EXAMPLE 10

Preparation of O,O-diethyl-O-[1-(4-chlorophenyl)-3-trifluoromethyl-5-pyrazoyl]phosphoric ester (Compound No. 18)

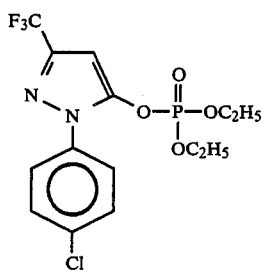

After 500 mg (1.91 mmol) of 1-(4-chlorophenyl)-3-trifluoromethyl-5-hydroxypyrazole, 330 mg (1.91 mmol) of diethylchlorophosphate and 600 mg (4.4. mmol) of potassium carbonate were added to 15 ml of acetonitrile and stirred, the resultant solution was reacted at a temperature of 50° to 60° C. for 2 hours. Hereinafter the procedure was the same as in Example 2, and then 540 mg (72% of theoretical) of the yellowish colored above-indicated product was obtained.

$^1$H NMR(CDCl$_3$): δ=7.5(m, 4H), 6.4(s, 1H), 4.2(q, 4H), 1.3(t, 6H).

Mass: m/e=398

EXAMPLE 11

Preparation of O,O-diethyl-O-[1-(4-chlorophenyl)-3-trifluoromethyl-5-pyrazoyl]thiophosphoric ester (Compound No. 20)

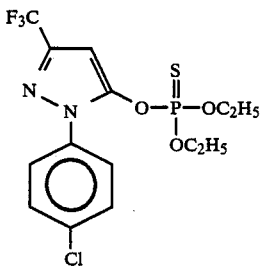

After 500 mg (1.91 mmol) of 1-(4-chlorophenyl)-3-trifluoromethyl-5-hydroxypyrazole, 360 mg (1.91 mmol) of diethylchlorothiophosphate and 600 mg (4.4. mmol) of potassium carbonate were added to 15 ml of acetonitrile and stirred at room temperature, the resultant solution was reacted at a temperature of 50° to 60° C. for 2 hours. Hereinafter the procedure was the same as in Example 3, and then 680 mg (86% of theoretical) of the yellowish colored above-indicated product was obtained.

$^1$H NMR(CDCl$_3$): δ=7.5(m, 4H), 6.4(s, 1H), 4.2(q, 4H), 1.3(t, 6H).

Mass: m/e=414.5

EXAMPLE 12

Preparation of O,O-diethyl-O-[1-(2,4-dichlorophenyl)-3-trifluoromethyl-5-pyrazoyl]phosphoric ester (Compound No. 22)

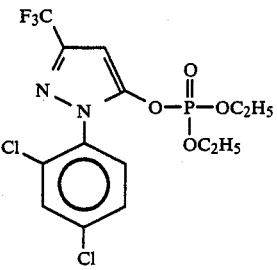

After 400 mg (1.35 mmol) of 1-(2,4-dichlorophenyl)-3-trifluoromethyl-5-hydroxypyrazole, 240 mg (1.35 mmol) of diethylchlorophosphate and 400 mg (2.7 mmol) of potassium carbonate were dissolved in 15 ml of acetonitrile, the resultant solution was reacted at a temperature of 50° to 60° C. for 2 hours. Hereinafter the procedure was the same as in Example 2, and then 400 mg (68% of theoretical) of the yellowish colored above-indicated product was obtained.

$^1$H NMR(CDCl$_3$): δ=7.3(m, 3H), 6.3(s, 1H), 4.1(q, 4H), 1.3(t, 6H).

Mass: m/e=432

EXAMPLE 13

Preparation of O,O-diethyl-O-[1-(2,4-dichlorophenyl)-3-trifluoromethyl-5-pyrazoyl]thiophosphoric ester (Compound No. 24)

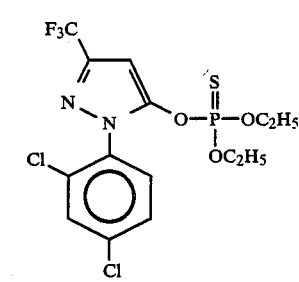

After 400 mg (1.35 mmol) of 1-(2,4-dichlorophenyl)-3-trifluoromethyl-5-hydroxypyrazole, 255 mg (1.35 mmol) of diethylchlorothiophosphate and 400 mg (2.7 mmol) of potassium carbonate were added to 15 ml of acetonitrile and stirred at room temperature, the resultant solution was reacted at a temperature of 50° to 60° C. for 2 hours. Hereinafter the procedure was the same as in Example 3, and then 450 mg (75% of theoretical) of the yellowish colored above-indicated product was obtained.

$^1$H NMR(CDCl$_3$): δ=7.3(m, 3H), 6.3(s, 1H), 4.1(q, 4H), 1.3(t, 6H).

Mass: m/e=448

EXAMPLE 14

Preparation of O,O-diethyl-O-(4-chloro-1-methyl-3-trifluoromethyl-5-pyrazoyl) phosphoric ester (Compound No. 26)

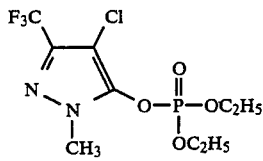

As a result of following the same method as in Example 2 except that 2.0 g of 4-chloro-1-methyl-3-trifluoromethyl-5-hydroxypyrazole instead of 1-methyl-3-trifluoromethyl-5-hydroxypyrazole was used, 3.2 g of the above-indicated product was obtained.

$^1$H NMR(CDCl$_3$): δ=4.30(t, 4H), 3.85(s, 3H), 1.36(t, 6H).
Mass: m/e=332.6

EXAMPLE 15

Preparation of O,O-diethyl-O-(4-chloro-1-methyl-3-trifluoromethyl-5-pyrazoyl)thiophosphoric ester (Compound No. 29)

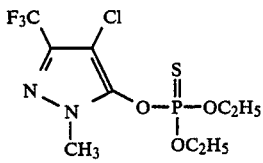

As a result of following the same method as in Example 4 except that 0.4 g (1.99 mmol) of 4-chloro-1-methyl-3-trifluoromethyl-5-hydroxypyrazole instead of 1-methyl-3-trifluoromethyl-5-hydroxypyrazole was used, 0.62 g (88% of theoretical) of the above-indicated product was obtained.

$^1$H NMR(CDCl$_3$): δ=1.3(t, 6H), 3.7(s, 3H), 4.1(m, 4H).
Mass: m/e=353

EXAMPLE 16

Preparation of O,O-diethyl-O-(4-chloro-1-phenyl-3-trifluoromethyl-5-pyrazoyl)phosphoric ester (Compound No. 33)

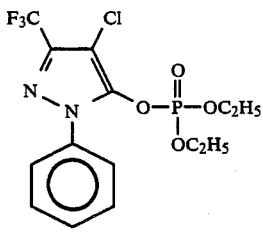

<Method 1> 728 mg (2 mmol) of Compound No. 12 and 297 mg (2.2 mmol) of NCS(N-chlorosuccinimide) were dissolved in 10 ml of chloroform, and a little benzoylperoxide was added thereto. After the resultant solution was reacted at 60° C. for 8 hours, the solvent was removed under reduced pressure and 10 ml of ether was added. The resultant solid was removed, and the ether solution was concentrated under reduced pressure and purified by column chromatography on silica-gel. Consequently, 509 mg (64% of theoretical) of the yellowish above-indicated product was obtained.

$^1$H NMR(CDCl$_3$): δ=1.3(t, 6H), 4.2(q, 4H), 7.2-7.6(m, 5H).
Mass: m/e=398

<Method 2> As a result of following the same method as in Example 2 except that 525 mg (2 mmol) of 4-chloro-1-phenyl-3-trifluoromethyl-5-hydroxypyrazole instead of 1-methyl-3-trifluoromethyl-5-hydroxypyrazole was used, 692 mg (87% of theoretical) of the above-indicated product was obtained.

EXAMPLE 17

Preparation of O,O-diethyl-O-(4-chloro-1-phenyl-3-trifluoromethyl-5-pyrazoyl)thiophosphoric ester (Compound No. 36)

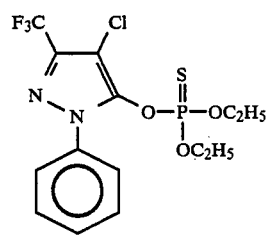

<Method 1> As a result of following the same method as method 1 of Example 16 except that 760 mg (2 mmol) of Compound No. 15 instead of 728 mg (2 mmol) of Compound No. 12 was used, 587 mg (71% of theoretical) of the above-indicated product was obtained.

$^1$H NMR(CDCl$_3$): δ=1.3(t, 6H), 4.2(q, 4H), 7.5(m, 5H).
Mass: m/e=414

<Method 2> As a result of following the same method as in Example 4 except that 525 mg (2 mmol) of 4-chloro-1-phenyl-3-trifluoromethyl-5-hydroxypyrazole instead of 1-methyl-3-trifluoromethyl-5-hydroxypyrazole was used, 679 mg (82% of theoretical) of the above-indicated product was obtained.

The 5-hydroxypyrazoles shown by the formula (II) wherein R$^1$ is hydrogen employed as a starting material can be prepared in accordance with the methods for preparing 1-methyl-5-hydroxy-3-trifluoromethylpyrazole (; 1-methyl-5-hydroxy-5-trifluoromethyl-5-pyrazolone) [Ref.: (1) H. Dorn, Chem. Heterocycl. Compd. (Engl. Transl.) 16, 1 (1980). (2) George De Stevens et al., J. Am. Chem. Soc., 81, 6292 (1959).]

Also, the 5-hydroxypyrazoles shown by the formula (II) wherein R$^1$ is a halogen selected from the group consisting of bromine, chlorine and iodine, can be prepared by halogenating the foregoing 5-hydroxypyrazoles shown by the formula (II) wherein R$^1$ is a hydrogen, using typical halogenating reagents.

Examples of the 5-hydroxypyrazoles of the formula (II) which can be prepared by the above methods are given in Table 2.

TABLE 2

F₃C—[pyrazole]—R¹, OH, N-N-R⁴

| Compound No. | R¹ | R⁴ | m.p. (°C.) | m/e |
|---|---|---|---|---|
| 51 | H | CH₃ | 131 | 166 |
| 52 | H | C₆H₅ | 185~187 | 228 |
| 53 | H | —C₆H₄—Cl | 81~82 | 262 |
| 54 | H | —C₆H₃Cl₂ | 230 | 296 |
| 55 | H | —C₆H₄—NO₂ | 72~73 | 273 |
| 56 | H | C(CH₃)₃ | 162~163 | 208 |
| 57 | Cl | CH₃ | 155 | 200 |
| 58 | Br | CH₃ | 142 | 245 |
| 59 | Cl | —C₆H₅ | 70 | 262 |

In the above Table 2, Compounds No. 53 to 59 are new chemcals, and they can be also prepared by the same methods as Compound 51 and 52. Examples of their preparation are as follows.

EXAMPLE 18

Preparation of 4-chloro-5-hydroxy-1-methyl-3-trifluoromethyl-pyrazole (Compound No. 57)

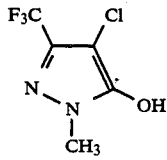

After 2 g (12 mmol) of 5-hydroxy-1-methyl-3-trifluoromethylpyrazole and 1.76 g (13 mmol) of NCS were dissolved in 20 ml of chloroform, the resultant solution was reacted at 60° C. for 6 hours. At the completion of the reaction, the solvent was removed and 10 ml of ether was added. Said solution was shaken and filtered to remove resultant solids. The residual solution was then concentrated to obtain a crude product. The resultant crude product was pruified by column chromatography on silica-gel using a developing solvent (1:3) of ethylacetate and hexane, and 1.98 g (83% of theoretical) of the above-indicated product was obtaind as a white colored solid.

¹H NMR(CDCl₃): δ=3.6(s, 3H), 8.9(broad s, 1H).
Mass: m/e=200
Rf(hexane/ethylacetate=1/1)=0.45
m.p.=155°–156° C.

EXAMPLE 19

Preparation of 4-bromo-5-hydroxy-1-methyl-3-trifluoromethyl-pyrazole (Compound No. 58)

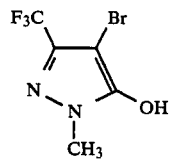

As a result of following the same method as in Example 18 except that NBS(N-bromosuccinimide) instead of NCS was used, the above-indicated product was obtained (77% yield of theoretical).

¹H NMR(CDCl₃): δ=3.6(s, 3H), 8.7(broad s, 1H),
Mass: m/e=245
Rf(hexan/ethylacetate=1/1)=0.50
m.p.=142°–143° C.

EXAMPLE 20

Preparation of 4-chloro-5-hydroxy-1-phenyl-3-trifluoromethyl-pyrazole) (Compound No. 59)

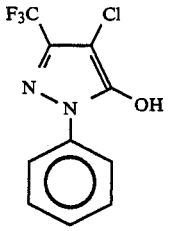

As a result of following the same method as in Example 18 except that 500 g (2.2 mmol) of 5-hydroxy-1-phenyl-3-trifluoromethylpyrazole instead of 5-hydroxy-1-methyl-3-trifluoromethylpyrazole was used, 398 mg (69% of theoretical) of the pure above-indicated product was obtained.

Mass: m/e=262
m.p.=70° C.

And also, the present invention is directed to the insecticidal compositions comprising the insecticidal compound of the present invention as an active compound. Said insecticidal compositions can be formulated in various forms, such as aqueous dispersions, emulsions, dusts, granules and so forth. These compositions are preferred to comprise one or more active compounds of the present invention with one or more suitable adjuvants such as carriers and diluents which are chemically inert to the active compound.

The exact concentration of the active compound in a composition thereof with an adjuvant therefor can vary; it is only necessary that the active compounds be present in sufficient amounts so as to make possible the application of an insecticidally effective dosage. For example, in the case that the compositions are emulsions or aqueous dispersions, the amount of the active compound is preferred to range from 10 to 90% by weight.

And in the case of dust compositions, said amount is preferred to range from 0.1 to 30% by weight, also in the case of granule compositions, the amount is preferred to range from 1 to 30% by weight. But, the amount of the active compound in the compositions is somewhat variable according to the purpose of use of the compositions.

Preferred carriers to be employed in the compositions according to the present invention are liquid carriers which are selected from alcohols (i.e. monohydric alcohols like methanol, dihydric alcohols like ethyleneglycol, and trihydric alcohols like glycerine, etc.), ketones (i.e. acetone, methylethylketone, etc.), ethers (i.e. dioxane, tetrahydrofuran, cellosolve, etc.), aliphatic hydrocarbons (i.e. gasoline, kerosene, etc.), hydrocarbon halides (i.e. chloroform, carbon tetrachloride, etc.), acid amides (i.e. dimethylformamide, etc.), esters (i.e. butyl acetate, ethyl acetate, glyceride, etc.) and nitriles (i.e. acetonitrile, etc.), and solid carriers which are selected from mineral particles such as kaoline, clay, bentonite, acid clay, talc, diatomaceous earth, silica and sand, and vegetable powers such as arbor. Said liquid carriers can be used separately or in company with one or more other liquid carriers.

The insecticidal composition of the present invention may include emulsifying agents, spreaders, dispersing agents or permeating agents. Also, the composition may include nonionic, anionic or cationic surfactants, for example, fatty acid soda or polyoxyalkylesters, alkylsulfonates or polyethyleneglycolethers.

On the other hand, one of the compounds of the present invention or compositions containing the same, can be advantageously employed in combination with one or more additional pesticidal compounds which are active agricultural chemicals. Such additional pesticidal compounds may be insecticides, herbicides, plant hormones and sterilizers, and if necessary, fertilizers.

| Composition 1 (Emulsion) | |
|---|---|
| Compound No. 14 | 20% (by weight) |
| xylene | 75% |
| polyoxyethyleneglycolether | 5% |

The foregoing components were mixed to form an emulsion composition.

| Composition 2 (Dusts) | |
|---|---|
| Compound No. 15 | 5% (by weight) |
| kaolin | 94.6% |
| silicon (antifoaming agent) | 0.3% |
| polyoxyethyleneglycolether | 0.1% |

The foregoing components were mixed to form a dust composition.

| Composition 3 (Aqueous dispersion) | |
|---|---|
| Compound No. 8 | 30% (by weight) |
| sodium lignosulfonate | 5% |
| polyoxyethyleneglycolether | 5% |
| bentonite | 60% |

The foregoing components were mixed to form an aqueous dispersion composition.

| Composition 4 (Granules) | |
|---|---|
| Compound No. 14 | 10% (by weight) |
| sodium lignosulfonate | 5% |
| bentonite | 85% |

The foregoing components were kneaded along with water and formed into a granule composition.

To demonstrate the superior effect of the compounds which were prepared in accordance with the present invention, test solutions with 250 ppm were prepared for the first insecticidal tests unless otherwise specifies. The insecticidal rates (%) were calculated from these solutions. In the case of an insecticidal rate of 100%, the concentration of the test solution was gradually reduced until the $LC_{50}$ value, namely that concentration (ppm) which gives an insecticidal rate of 50%, was determined.

TEST 1

Insecticidal test for Brown plant hopper

Brown plant hoppers (Nilaparvata lugens stal), susceptive strain, were successively reared using Dongjin-rice plants. Four days after emergence, the female adults thereof were tested.

For the insecticidal test, six rice seedlings 5~7 cm in length were wrapped with absorbent cotton and inserted into a cylinder of 3 cm in diameter and 15 cm in height. 20 female adults were inoculated therein, and a test solution (250 ppm) prepared previously was applied twice with a microspray nozzle (volume of one application: 0.0254±0.0005 ml). The cylinder was placed in an incubator with a temperature of 25±1° C., a relative humidity of 50±5%, and light conditions of 16 h light and 8 h dark. After 24 hours, the number of killed plant hoppers was examined to determine the insecticidal rate (%).

The results are shown in Table 3.

TABLE 3

| Compound No. | Insecticidal Rate (%) | Compound No. | Insecticidal Rate (%) |
|---|---|---|---|
| 3 | 100 | 15 | 100 |
| 4 | 100 | 20 | 100 |
| 7 | 100 | 26 | 100 |
| 8 | 100 | 29 | 100 |
| 9 | 77 | 36 | 100 |
| 11 | 55 | 42 | 100 |
| 12 | 85 | 43 | 100 |
| 14 | 95 | Untreated | 0 |

And, those compounds which produced an insecticidal rate of 100% at 250 ppm, the first test concentration, were tested again with gradually reduced concentrations to determine the $LC_{50}$ value.

The results are shown in Table 4.

TABLE 4

| Compound No. | 3 | 4 | 8 | 15 | 42 | 43 |
|---|---|---|---|---|---|---|
| $LC_{50}$ (ppm) | 60.3 | 18.8 | 8.3 | 18.4 | 26.1 | 27.5 |

TEST 2

Insecticidal test for Green peach aphid

Green peach aphides (Myzus persicae sulzer) were successively reared using tobacco plants (Variety: NC-82), and the apterous larvae thereof were tested.

For the insecticidal test, a piece of tobacco leaf 9 cm in diameter was dipped in the test solution for 30 seconds. After air-drying it for 30 minutes, the dried piece of tobacco leaf was put in a petri dish. 20 apterous larvae were inoculated therein, and treated tobacco leaf was placed in an incubator. After 24 hours, the number of killed aphides was examined to determine the insecticidal rate (%).

The results are shown in Table 5.

TABLE 5

| Compound No. | 4 | 8 | 9 | 12 | 15 | 20 | 29 | 43 | Untreated |
|---|---|---|---|---|---|---|---|---|---|
| Insecticidal Rate (%) | 82 | 100 | 100 | 75 | 100 | 78 | 40 | 90 | 0 |

TEST 3

Insecticidal test for Diamond-back moth

Diamond-back moths (Plutella Xylostella Linnaeus) were successively reared using cabbages, and third instar larvae thereof were tested.

For the insecticidal test, a piece of cabbage leaf 9 cm in diameter was dipped in a test solution for 30 minutes and air-dried for 30 minutes. The dried piece of tobacco leaf was put in a petri dish, and 10 of the third instar larvae were inoculated therein. The petri dish was capped and placed in an incubator. After 24 hours, the number of killed moths was examined to determine the insecticidal rate (%).

The results are shown in Table 6.

TABLE 6

| Compound No. | Insecticidal Rate (%) | Compound No. | Insecticidal Rate (%) |
|---|---|---|---|
| 4 | 20 | 22 | 100 |
| 8 | 35 | 24 | 100 |
| 11 | 100 | 29 | 50 |
| 12 | 100 | 33 | 100 |
| 14 | 100 | 36 | 100 |
| 15 | 100 | 42 | 5 |
| 18 | 95 | 43 | 10 |
| 20 | 100 | Untreated | 0 |

Those compounds which produced an insecticidal rate of 100% at 250 ppm and, for comparison, commercial insecticides were tested according to the method mentioned above, and the $LC_{50}$ values were determined.

The results are shown in Table 7.

TABLE 7

| Compound No. | $LC_{50}$ (ppm) | Compound No. | $LC_{50}$ (ppm) |
|---|---|---|---|
| 11 | 24.4 | 33 | 78.4 |
| 12 | 4.0 | 36 | 11.2 |
| 14 | 0.8 | *DDVP | 118.0 |
| 15 | 0.8 | *Fenitrothron | 122.4 |
| 18 | 65.5 | *BPMC | 130.7 |
| 20 | 37.9 | *Fenvalerate | 13.0 |
| 22 | 24.4 | *Permethrin | 11.2 |
| 24 | 59.5 | *Deltamethrin | 6.3 |

*commercial insecticides.

TEST 4

Insecticidal test for the Common mosquito

Common mosquitos (Culex pipiens pallens) were successively reared and third instar larvae thereof were tested.

The test solution was added to 100 ml of distilled water to make 0.1 ppm solution, and 20 of the third instar larvae were inoculated therein. After 24 hours, the number of killed mosquitos was examined to determine the insecticidal rate (%).

The results are shown in Table 8.

TABLE 8

| Compound No. | Insecticidal Rate (%) | Compound No. | Insecticidal Rate (%) |
|---|---|---|---|
| 3 | 60 | 14 | 100 |
| 7 | 100 | 15 | 100 |
| 8 | 100 | 20 | 100 |
| 11 | 85 | 24 | 100 |
| 12 | 100 | 36 | 100 |
|  |  | Untreated | 0 |

Those compounds which produced an insecticidal rate of 100% of 0.1 ppm and commercial insecticides were tested according to the method mentioned above to determine the $LC_{50}$ values.

The results are shown in Table 9.

TABLE 9

| Compound No. | $LC_{50}$ (ppm) | Compound No. | $LC_{50}$ (ppm) |
|---|---|---|---|
| 8 | 0.0039 | 24 | 0.0024 |
| 12 | 0.0057 | 36 | 0.0180 |
| 15 | 0.0038 | *Permethrin | 0.0008 |
| 20 | 0.0083 | *DDVP | 0.0210 |

*commercial insecticides.

TEST 5

Insecticidal test for Bean bug

Bean bugs (Riptortus clavatus thunberg) were successively reared in an incubator, and third instar larvae thereof were tested.

For the insecticidal test, three soybean seedlings which had germinated in a vermiculite culture medium, were dipped in a test solution for 30 seconds and air-dried for 30 minutes. The dried seedlings were put in a polyethylene vessel 6 cm in diameter and 3.5 cm in height. 10 of the third instar larvae were inoculated therein, the vessel was capped and placed in an incubator. After 24 hours, the number of killed bugs was examined to determine the insecticidal rate (%).

The results are shown in Table 10.

TABLE 10

| Compound No. | 4 | 8 | 26 | 29 | Untreated |
|---|---|---|---|---|---|
| Insecticidal Rate (%) | 100 | 100 | 70 | 100 | 0 |

TEST 6

Insecticidal test for Tobacco cutworm

Tobacco cutworms (Spodoptera litura) were successively reared using cabbages, and third instar larvae thereof were tested.

For the insecticidal test, a piece of cabbage leaf 9 cm in diameter was dipped in a test solution for 30 seconds and air-dried for 30 minutes. The dried piece of cabbage leaf was put in a petri dish 9 cm in diameter, and 10 of the third instar larvae were inoculated therein. The petri dish was placed in an incubator, and after 24 hours, the number of killed cutworms was examined to determine the insecticidal rate (%).

The results are shown in Table 11.

TABLE 11

| Compound No | 14 | 15 | Untreated |
|---|---|---|---|
| Insecticidal Rate (%) | 35 | 100 | 0 |

From the results of said tests, it is demonstrated that the 5-hydroxypyrazole derivatives of the present invention exhibit better bioactivity in comparison with, for example, the compound which is proposed in Korean patent publication No. 84-225. And also, the present 5-hydroxypyrazole derivatives exhibit particularly against the Diamond-back moth an excellent insecticidal effect which is more than 8 fold that of Deltamethrin which is known as one of the best insecticides of the existing pyrethroid compounds.

What is claimed is:

1. A compound corresponding to the formula (I)

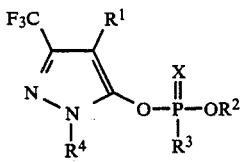

wherein
- $R^1$ represents hydrogen, or a halogen atom selected from the group consisting of bromine, chlorine and iodine;
- $R^2$ represents a lower alkyl group;
- $R^3$ represents an alkoxy, lower alklythio, phenoxy or thiophenoxy group;
- $R^4$ represents hydrogen, a lower alkyl, or substituted or unsubstituted phenyl group; and
- X represents oxygen or sulfur;

wherein the lower alkyl group is a $C_{1-6}$ straight or branched alkyl group.

2. A compound as defined in claim 1 wherein $R^1$ is hydrogen.

3. A compound as defined in claim 2 wherein X is sulfur.

4. The compound as defined in claim 3 which is O,O-dimethyl-O-(1-phenyl-3-trifluoromethyl-5-pyrazoyl)-thiophosphoric ester.

5. The compound as defined in claim 3 which is O,O-diethyl-O-(1-phenyl-3-trifluoromethyl-5-pyrazoyl)thiophosphoric ester.

6. The compound as defined in claim 3 which is O,O-diethyl-O-(1-methyl-3-trifluoromethyl-5-pyrazoyl)thiophosphoric ester.

7. An insecticidal composition comprising an inert carrier, a diluent and a surfactant with an active compound corresponding to the formula (I)

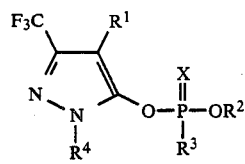

wherein
- $R^1$ represents hydrogen, or a halogen atom selected from the group consisting of bromine, chlorine and iodine;
- $R^2$ represents a lower alkyl group;
- $R^3$ represents an alkoxy, lower alklythio, phenoxy or thiophenoxy group;
- $R^4$ represents hydrogen, a lower alkyl, or substituted or unsubstituted phenyl group; and
- X represents oxygen or sulfur;

wherein the lower alkyl group is a $C_{1-6}$ straight or branched alkyl group.

8. A composition as defined in claim 7 wherein $R^1$ is hydrogen.

9. A composition as defined in claim 8 wherein X is sulfur.

10. The composition as defined in claim 9 wherein the active compound is O,O-dimethyl-O-(1-phenyl-3-trifluoromethyl-5-pyrazoyl)thiophosphoric ester.

11. The composition as defined in claim 9 wherein the active compound is O,O-diethyl-O-(1-phenyl-3-trifluoromethyl-5-pyrazoyl)thiophosphoric ester.

12. A method for the kill and control of insects which comprises using a composition comprising an inert carrier, a diluent and a surfactant with an active compound corresponding to the formula (I)

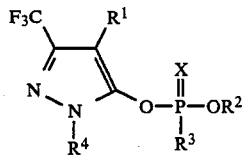

wherein
- $R^1$ represents hydrogen, or a halogen atom selected from the group consisting of bromine, chlorine and iodine;
- $R^2$ represents a lower alkyl group;
- $R^3$ represents an alkoxy, lower alklythio, phenoxy or thiophenoxy group;
- $R^4$ represents hydrogen, a lower alkyl, or substituted or unsubstituted phenyl group; and
- X represents oxygen or sulfur;

wherein the lower alkyl group is a $C_{1-6}$ straight or branched alkyl group.

13. A method as defined in claim 12 wherein $R^1$ is hydrogen.

14. A method as defined in claim 13 wherein X is sulfur.

15. The method as defined in claim 14 wherein the active compound is O,O-dimethyl-O-(1-phenyl-3-trifluoromethyl-5-pyrazoyl)thiophosphoric ester.

16. The method as defined in claim 14 wherein the active compound is O,O-diethyl-O-(1-phenyl-3-trifluoromethyl-5-pyrazoyl)thiophosphoric ester.

17. The method as defined in claim 14 wherein the active compound is O,O-diethyl-O-(1-methyl-3-trifluoromethyl-5-pyrazoyl)thiophosphoric ester.

* * * * *